United States Patent [19]
Boucot et al.

[11] Patent Number: 5,755,841
[45] Date of Patent: *May 26, 1998

[54] PROCESS AND DEVICE FOR MANUFACTURING SYNTHESIS GAS AND APPLICATION

[75] Inventors: Pierre Boucot, Ternay; Paul Gateau, Saint Jean de Boisseau; Jerome Weill, Lyons, all of France

[73] Assignee: Institut Francais du Petrole, Rueil Malmaison, France

[*] Notice: The term of this patent shall not extend beyond the expiration date of Pat. No. 5,632,787.

[21] Appl. No.: 631,909

[22] Filed: Apr. 12, 1996

Related U.S. Application Data

[63] Continuation of Ser. No. 341,163, Nov. 18, 1994, which is a continuation of Ser. No. 984,833, Dec. 3, 1992, abandoned.

[30] Foreign Application Priority Data

Dec. 3, 1991 [FR] France .................... 91 15060

[51] Int. Cl.$^6$ .................................. C01B 3/24
[52] U.S. Cl. ........................... 48/127.7; 48/198.7
[58] Field of Search ..................... 48/198.7, 198.8, 48/212, 215, 127.7, 127.9; 252/373

[56] References Cited

U.S. PATENT DOCUMENTS

| | | |
|---|---|---|
| 2,171,596 | 9/1939 | Parker . |
| 2,220,849 | 11/1940 | Riblett ............... 48/198.7 |
| 2,482,866 | 9/1949 | Phinney ............. 48/198.7 |
| 2,585,737 | 2/1952 | Carpenter .......... 48/198.7 |
| 2,635,952 | 4/1953 | D'Ouville .......... 48/198.7 |
| 2,655,442 | 10/1953 | Mayland ............ 48/127.9 |
| 2,767,233 | 10/1956 | Mullen et al. ..... 48/215 |
| 2,942,958 | 6/1960 | Dwyer ................ 48/198.7 |
| 2,943,062 | 6/1960 | Mader ................ 48/127.7 |
| 2,951,749 | 9/1960 | Bartholome et al. ... 48/198.7 |
| 3,477,824 | 11/1969 | Reed .................. 48/127.9 |
| 4,973,453 | 11/1990 | Agee .................. 48/198.7 |
| 5,106,590 | 4/1992 | Hopper et al. .... 48/198.8 |
| 5,632,787 | 5/1997 | Boucot et al. .... 48/198.7 |

FOREIGN PATENT DOCUMENTS

| | | |
|---|---|---|
| 0303438 | 2/1989 | European Pat. Off. . |
| 489995 | 7/1949 | France . |
| 552748 | 12/1956 | France . |
| 2638443 | 5/1990 | France . |
| 702035 | 1/1954 | United Kingdom ...... 48/198.7 |
| 775334 | 5/1957 | United Kingdom . |

*Primary Examiner*—Christopher Upton
*Attorney, Agent, or Firm*—Antonelli, Terry, Stout & Kraus, LLP

[57] ABSTRACT

The present invention relates to a process and to a device for manufacturing synthetic gas.

The reactor in accordance with the invention comprises within a single housing:
- a non catalytic combustion chamber (1) comprising at least one fuel injection element (2) and at least one oxidizer injection element (3) so as to achieve a partial combustion in said chamber referred to as "sufficient residence time chamber", and
- at least one catalytic bed (4) into which the gases coming from combustion chamber (1) run, and further comprising at least one additional oxidizer injection element (6) and at least one fuel injection element (7).

The reactor and the process in accordance with the invention may be applied to any chemical manufacturing utilizing synthetic gas.

6 Claims, 1 Drawing Sheet

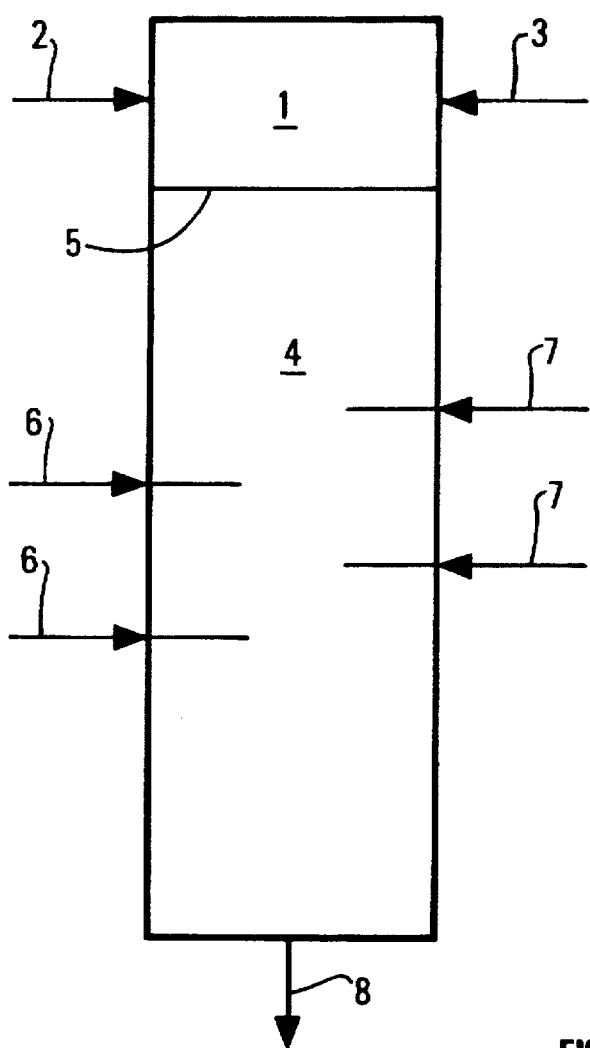
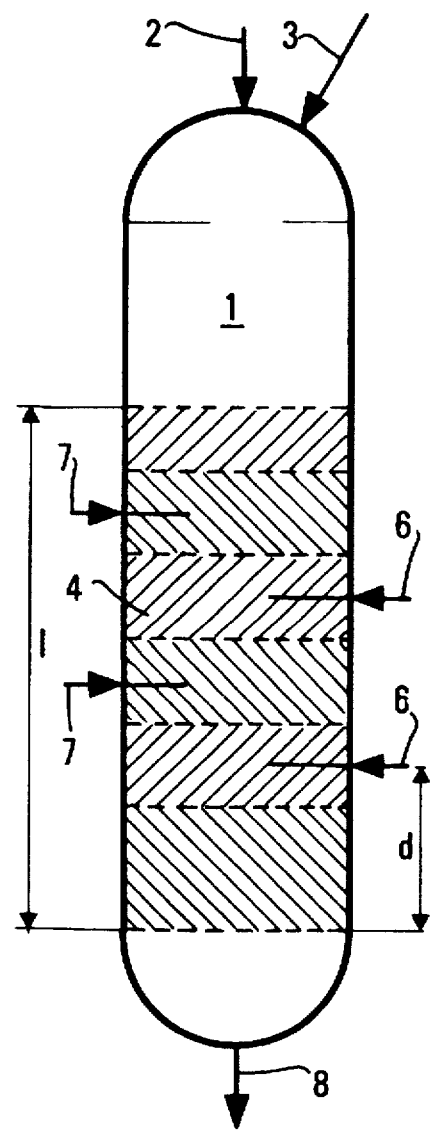
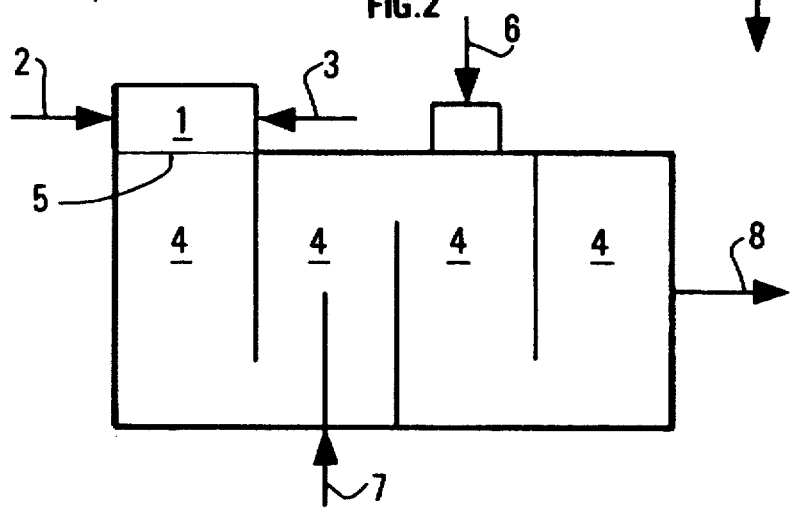

PROCESS AND DEVICE FOR MANUFACTURING SYNTHESIS GAS AND APPLICATION

This application is a continuation application of application Ser. No. 08/341,163, filed Nov. 18, 1994, which application is a continuation application of application Ser. No. 07/984,833, filed Dec. 3, 1992 (now abandoned).

BACKGROUND OF THE INVENTION

The present invention relates to a process and to a device for manufacturing synthetic gas, which may be used for producing for example: ammonia, methanol, urea, hydrocarbons, etc.

The gases obtained in accordance with the invention may be converted and then possibly purified or be used as reducing gases.

Synthetic gas is conventionally obtained through the reaction of a mixture of hydrocarbons or fuel with an oxidant.

A first way to produce synthetic gas consists of associating a primary reforming with a secondary reforming. The primary reforming reactor is conventionally made up of tubes filled with a catalyst and heated either through external combustion, or through heat exchange with warm effluents, for example with those of the secondary reforming reactor. The hydrocarbon is generally introduced into the primary reforming reactor with high steam excess.

The effluents resulting from the primary reforming are then introduced into the secondary reformer, which is also supplied with oxidant.

U.S. Pat. No. 3,278,452 describes a secondary reformer whose improvement consists in an additional introduction of oxidant between catalytic beds arranged successively in the reactor. However, the improvement provided by the stepped lay-out of the oxidant does not solve the main drawback of this type of reactors which requires a high amount of steam whose production is costly. Moreover, the drawback of steam excess is to change the distribution between the hydrogen, the carbon dioxide and the carbon monoxide present in the synthetic gas.

Another way to manufacture synthetic gas, with a low steam consumption, consists of achieving partial oxidation of the hydrocarbons.

U.S. Pat. No. 4,699,631 shows such an example of a reactor working without a catalyst, by means of a flame. However, this type of reactor always produces a certain amount of soot due to combustion under lack of oxygen, when afterwards requires a costly scrubbing. Besides, if the amount of soot is to be decreased, the oxygen consumption has to be increased, which reduces the reactor efficiency. Thus, although working with little steam, the drawback of this type of reactor is to produce soots when the oxygen consumption is decreased or when working in air.

Besides, the applicant has protected, by means of patent application EN.91/09,214, a reactor of the type defined at the beginning of the description and comprising a chamber referred to as "short residence time chamber", that is to say such that $V<0.4$ $D/P$; V being the inner volume of the chamber; D being the overall weight flow entering the combustion chamber; P being the pressure prevailing inside the chamber. The object of such a reactor is to reduce steam and cost requirements.

However, for reactors whose combustion chamber volume is too small, the fuel and oxidizer jets might lead to an erosion of the surfaces towards which they are projected, after several thousand hours of operation.

SUMMARY OF THE INVENTION

The object of the invention is to propose a synthetic gas reactor whose combustion chamber volume is sufficient to avoid this type of erosion.

Besides, in order to have a reactor requiring little steam, it appeared necessary, when the volume of the combustion chamber is relatively large, to introduce successively additional fuel and then oxidizer into the catalytic bad located downstream from the combustion chamber.

The invention thus relates to a reactor for manufacturing synthetic gas and comprising within a single housing:
- a non catalytic combustion chamber comprising at least one fuel injection element and at least one oxidizer injection element so as to achieve a partial combustion in said chamber, and
- at least one catalytic bed into which the gases coming from the combustion chamber run, and further comprising successively, in the direction of flow of the gases, at least one additional fuel injection element and at least one oxidizer injection element.

More particularly, the combustion chamber is such that:

$$V>0.4\ D/P$$

V being the inner volume of said chamber expressed in cubic meter,

D being the overall weight flow entering the chamber, expressed in kg/s, and

P being the pressure prevailing inside the chamber, expressed in megapascals.

Preferably, the fuel introduced into the combustion chamber and into the catalytic bed mainly consists of hydrocarbons which may be admixed with carbon oxides and/or hydrogen.

The oxidizer may be pure oxygen, or oxygen admixed with nitrogen, steam, carbon dioxide. The oxidizer may also be a mixture of oxygen and of another inert gas.

Preferably, the overall oxidizer supply, defined as the number of moles of oxygen contained in the oxidizer injected into the reactor in relation to the number of moles of carbon contained in the injected fuel, ranges between 0.3 and 0.65, and the same supply relative to the introduction of oxidizer in said combustion chamber ranges between 0.45 and 0.75.

Advantageously, the hydrogen/hydrocarbons ratio, defined as the molar ratio expressed in number of moles of hydrogen in relation to the number of moles of carbon of the fuel introduced into the combustion chamber, is less than 1.

Besides, steam may be introduced with the oxidizer and/or the fuel. The steam supply in the reactor, defined as the number of moles of water in relation to the number of moles of carbon, is less than 1.5.

The fuel may be preheated, before entering the combustion chamber, between 100° and 850° C., preferably between 600° and 700° C. The oxidant may be preheated at each inflow between 100° and 900° C., preferably between 135° and 750° C. The upper limit of this range (750° C.) may be lowered to 600° C., notably in cases where the oxidizer is oxygen or mainly pure oxygen.

The invention further relates to the process for manufacturing synthetic gas, which consists of performing within a single reactor:

partial conversion of a fuel in a non catalytic combustion chamber working under lack of oxidant; the fuel being introduced apart from the oxidant into said chamber, and additional oxidant supply at the level of a catalytic bed located downstream from said combustion chamber.

In particular, the process further consists of introducing fuel at the level of said catalytic bed upstream from the additional oxidant, and the inner volume V of said chamber is such that V>0.4 D/P D being the overall weight flow entering the combustion chamber, expressed in kg/s, P being the pressure prevailing inside the chamber, expressed in megapascals, and V being expressed in cubic meter.

The invention also relates to the application of the process and/or of the device to the production of methanol, ammonia, hydrocarbons, urea, acetic acid, hydrogen or a reducing gas.

BRIEF DESCRIPTION OF THE DRAWINGS

Other features and advantages of the invention will be clear from reading the following description given by way of non limitative example, with reference to the accompanying drawings in which:

FIG. 1 is a simplified longitudinal section of a vertical type reactor according to the invention, FIG. 2 is a simplified longitudinal section of a transverse type reactor according to the invention, FIG. 3 is a diagram of an embodiment example of the invention.

The same references will be used for the elements common to the various embodiments of the invention.

DESCRIPTION OF THE PREFERRED EMBODIMENTS

Thus, in accordance with these figures, the reactor is mainly made up of a combustion chamber 1 provided with at least two distinct inlets, one 2 allowing the fuel to be introduced, the other 3 injecting the oxidizer which is an oxidant.

Injection elements 2 and 3 do not only allow the fuel and the oxidizer to be introduced into said chamber 1, but also the combustion to be stabilized therein.

A partial combustion takes place in combustion chamber 1 and the effluents from this combustion run directly into the second part 4 of the reactor, which is filled with at least one catalytic bed.

The second part 4 of the reactor, also called catalyst or catalytic bed in the description hereafter, is part of the reactor since it shares a common surface 5 with combustion chamber 1. This surface is not necessarily horizontal.

Besides, catalytic bed 4 is provided with at least one inlet 6 for the additional oxidant and with at least one inlet 7 for the additional fuel. FIG. 1 shows two injectors 6 and two injectors 7, which constitutes a particular embodiment of the invention.

The first fuel injector 7 is advantageously located upstream from the first oxidizer injector 6, in relation to the direction of propagation of the gases in the reactor.

Finally, one or several outlets 8, located at the end of catalytic bed 4 in relation to the direction of flow of the gases in the reactor, are of course provided.

Injectors of any type known per se may be used to introduce the various components stated above.

The broad lines of the reactor according to the invention being given, it is now necessary to specify certain working conditions.

Combustion chamber 1 must make it possible to work with a sufficient residence time and under lack of oxidant.

One way to define the "sufficient" residence time may consist of imposing the following inequation:

V>0.4 D/P

V being the volume of chamber 1 expressed in cubic meter,

D being the overall weight flow entering chamber 1, expressed in kg/s, and

P being the predetermined operating pressure prevailing in chamber 1, expressed in megapascals.

As it is well-known by the man skilled in the art, and without the following description being considered as limitative, the catalysts used in accordance with the present invention are made up of:

a support based on oxides, having refractory properties and whose acidity has been neutralized, an active phase comprising 2 to 40%, preferably 3 to 30% by mass of at least one reducible metal M selected from nickel, cobalt, chromium, platinum metals. Taken separately, the proportion of platinum metals, if there are any, ranges between 0.01 and 1% by mass of the total above.

The support based on oxides comprises at least one simple or mixed oxide from the following list: alpha alumina; aluminate of spinel structure $NAl_2O_4$- $xAl_2O_3$ with x=0, 1, 2; at least one metal N selected from the list: magnesium, calcium, trontium, barium, potassium; aluminate of magnetoplumbite (or hexaaluminate) structure $NAl_{12}O_{19}$; N being a metal from the list above.

Besides, these supports may be possibly promoted by at least one metal P selected from silicium, potassium, uranium.

In the most severe thermal conditions, for example with mean temperatures higher than 1000° C., preferably higher than 1100° C. and most preferably higher than 1200° C., it may be advantageous to arrange at the top an attack layer consisting for example of chromium oxide or of a low proportion of nickel deposited on one of the supports cited above. This catalyst will protect the other catalyst located in the lower layer as described hereafter.

The catalysts used in the process according to the invention are prepared either by impregnation of the preformed support by a solution containing at least one metal M and possibly at least one metal P, drying and thermal activation; or by mixing of the precursors oxides of metal aluminum, M and N, possibly P, forming, drying and activation. Metal P, if used, may be added either before or after the forming stage.

They may finally also be prepared by coprecipitation or by the sol-gel process.

The catalysts used in the process according to the invention may exhibit the most varied geometries: pellets, balls, extrudates, annular pellets, ribbed rings, wheel-shaped catalysts from 3 to 30 mm. They may even be used in the form of monoliths, consisting either of the oxides and/or the metals corresponding to the metallic elements cited above, or of refractory steel monoliths coated with said elements. One or several monoliths may be present.

It goes without saying that, according to operating conditions, the charge used, the local composition, the presence or not of steam, the level of the risk of carbon deposition, such or such formula will be used. Thus, the catalysts promoted by potassium or strontium, or by potassium plus calcium, or else calcium will be preferably used when the risk of carbon deposition is the highest.

The present invention is preferably performed in the presence of at least one catalyst allowing the selective activation of the wanted reaction processes to be achieved, that is to:

1) selectively convert the methane and, if they are also present, the higher hydrocarbons, by direct or indirect reaction with the oxygen and/or the steam present, to carbon oxides and hydrogen, 2) activate the other reaction processes wanted and notably the conversion of the coke precursors, according to the reaction:

$$CH_x + H_2O \rightleftarrows CO + H_{(2+x)} \quad x \geq 0$$

3) allow disproportionation reactions of CO to be limited $$2 CO \rightleftarrows CO_2 + C$$

through the removal of the carbon formed, as above, 4) if $CO_2$ is at least partly recycled, selectively activate the reaction:

$$CH4 + CO_2 \rightleftarrows 2CO + 2H2$$

The catalysts known by the man skilled in the art and used equally in steam reforming, secondary reforming, partial catalytic oxidation processes are suitable on several accounts for the embodiment of the invention. It is however preferable that the catalysts used have a good thermal stability (for example up to at least 900° C. and preferably at least 1000° C.).

Besides, these catalysts may be arranged in one or several beds, laid out as described above and separated by one or several devices (6, 7) for injecting one or several gaseous compounds such as those described above.

The volumetric velocity per hour (VVH) with respect to hydrocarbon and expressed in NTP volumes of hydrocarbon per hour and per volume of catalyst may be expressed in corrected VVH. If m is the average number of atoms of carbon in the charge, the corrected VVH (which will be that used in the process of the invention) is:

corrected VVH=VVH×m.

A corrected VVH ranging between 200 and 10,000 $h^{-1}$, preferably between 400 and 8000, and most preferably between 500 and 7000 $h^{-1}$, is used.

It is obvious to the man skilled in the art that the catalyst bed can be parted in n bed of volumes $V_1, V_2, \ldots V_i \ldots V_n$, such that $V_1+V_2+\ldots+V_i+\ldots+V_n=v$, the VVH remaining expressed in relation to the overall catalyst volume v.

The fuel introduced through the inlet or inlets 2 of the combution chamber and through inlets 7 will preferably consist of hydrocarbons (natural gas or methane for example) admixed with carbon oxide (CO, $CO_2$) and/or with hydrogen and/or with inert gases.

Steam may also be admixed with the hydrocarbons, preferably in the proportion defined at the beginning of the description.

The proportion of hydrogen in the hydrocarbons is such that the $H_2$/hydrocarbons ratio is less than 1.

The composition of the gases injected at the various inlets is not necessarily identical.

The oxidant introduced at the level of inlet 3 may be pure oxygen, a mixture of oxygen and nitrogen, air, a mixture of oxygen and steam, a mixture of oxygen and carbon dioxide, a mixture of oxygen and of another inert gas.

The overall supply of steam and of carbon dioxide remains low in relation to certain other technologies of the prior art cited above. In fact, a molar ratio $$K = \frac{H_2O + CO_2}{C} < 1.5$$

will be preferably used, where C is the total carbon comprised in the hydrocarbons, and where ($H_2O + CO_2$) is the sum of the molar flow rates of water and $CO_2$ injected. By way of comparison, the same molar ratio for a conventional autothermic reactor would be higher than 2.

Having several oxidant inlets according to the invention allows the composition of the fuel and of the oxidant to be modulated at the various stages, and thus the reaction to be better controlled. For example, for the synthesis of ammonia, if the stoichiometry $N_2+3H_2$ is wanted, air will be introduced at the level of the catalytic bed through the inlet or the other inlets 6.

Preheating is recommended, both for the fuel and for the oxidant, before their introduction into the reactor. The fuel may be preferably preheated between 100° C. and 850° C., and the oxidant may be preheated between 100° C. and 900° C. More precisely, temperatures ranging between 200° C. and 750° C. are preferable.

The pressure in combustion chamber 1 ranges between 1 and 150 bars, preferably between 30 and 100 bars.

The significance of the present invention will be clear from comparing the examples hereafter. Example 1 gives results of the prior art, whereas examples 2 and 3 illustrate embodiments of the invention. In all the following examples, the reactor receives natural gas containing (by volume) 98.7% of methane, 0.9% of ethane and 0.4% of nitrogen.

EXAMPLE 1

It relates to a pilot reactor whose overall inner volume is 250 liters (chamber plus catalyst). This reactor is half filled with catalyst so as to leave a 125-liter free volume in the chamber.

The catalytic bed comprises at the top a first layer of a catalyst containing 3.8% of chromium on alpha alumina. This layer occupies 20% of the overall catalyst volume. The rest consists of a catalyst containing 8.8% of nickel also deposited on alpha alumina.

The combustion chamber is supplied with natural gas and oxygen, both admixed with steam and introduced at 777K. The natural gas contains 50% of its steam flow rate: the overall flow rate (steam plus natural gas) is about 150 $Nm^3/h$. The pure oxygen, whose flow rate is 58 $Nm^3/h$, is admixed with steam whose flow rate is 195 $Nm^3/h$.

The pressure in the reactor is 30 bars.

The temperature on the first catalyst layer is 1453K.

It has been possible to bring the flow rate of natural gas from 100 up to 112 $Nm^3/h$ (with 50 $Nm^3/h$ of steam) and the flow rate of steam introduced with the oxygen from 195 $Nm^3/h$ down to 170 $Nm^3/h$.

The temperature at the top of the bed is then 1476K.

The outlet composition is the following:

| | |
|---|---|
| $H_2$ | 42.8% |
| $CO_2$ | 7.2% |
| $CH_4$ | 0.6% |

| | |
|---|---|
| CO | 12.4% |
| H₂O | 37% |

With such a reactor, the steam flow cannot be decreased below 160 Nm³/h, regarding oxygen, without causing an increase in the pressure drop due to a load of soot in the catalyst.

EXAMPLE 2

The example above, according to the prior art, shows that it is not possible to reach a $H_2/CO$ ratio close to 2, which is a necessary condition for manufacturing higher hydrocarbons through processes of the Fisher-Tropsch type.

The reactor in accordance with this second example is identical to that of example 1, as well as the flow rates entering combustion chamber 1. Besides, the volumes of chamber 1 and of catalyst 4 remain unchanged.

However, four tubes 7 pierced with openings open into catalytic bed 4, at the two thirds of the height from outlet 8 onwards. These tubes are protected by a steam-cooled double jacket. In this part of the catalytic bed, the temperature is 1253K.

A mixture of 112 Nm³/h of natural gas and 22 Nm³/h of steam at 780K flows in through tubes 7. Cooling of the tubes through steam prevents coking in the tubes.

Besides, four tubes 6 pierced with openings open into bed 4, at half the height thereof. Contrarily to tubes 7 supplying natural gas, tubes 6 are made of alumina and are not cooled.

The catalytic bed at this level consists of a layer of catalyst with 3.8% of chromium.

A mixture of oxygen, steam and carbon dioxide, all preheated at 765K, flows in through tubes 6.

| | |
|---|---|
| O₂ flow | 65 Nm³/h |
| Steam flow | 24 Nm³/h |
| CO₂ flow | 62 Nm³/h |

At the reactor outlet, the temperature is about 1245K; the composition of the gases is the following:

| | |
|---|---|
| H₂ | 41.9% |
| CO₂ | 8.8% |
| CH₄ | 0.8% |
| CO | 19.4% |
| H₂O | 29.1% |

EXAMPLE 3

The reactor in accordance with example 2 may be modified so as to further decrease the necessary steam rate.

The reactor in accordance with example 3 is an embodiment of the invention exhibiting this feature. FIG. 3 illustrates this reactor.

Thus, the overall volume of the reactor is 250 l (0.25 m³). The volume of combustion chamber 1 is 80 liters.

At the level of combustion chamber 1, gas is introduced at a flow rate of 75 Nm³/h and steam is introduced at a flow rate of 135 Nm³/h through inlet 2 intended for natural gas. The temperature of the mixture introduced is about 773K. A mixture of oxygen, at a flow rate of 45 Nm³/h, and of steam, at a flow rate of 135 Nm³/h, is introduced through inlet 2 intended for the oxidant, the mixture being brought to a mean temperature of 793K.

In catalyst 4, four introduction levels are provided:

At the level which is closest to combustion chamber 1, a mixture of natural gas (flow rate of about 85 Nm³/h) and of steam (flow rate of about 17 Nm³/h) is introduced at a temperature close to 773K. Four tubes 7 may be provided, at 90° in relation to one another, to inject this mixture.

Four other tubes open into a second level of the catalytic bed, all of them being located at the same distance from the first level. These tubes 6 allow a mixture of oxygen and of steam to be introduced at about 673K. The flow rate of oxygen is preferably 47 Nm³/h, and the flow rate of steam is close to 25 Nm³/h.

Preferably, tubes 6 located at this second level are angularly equidistant and, moreover, they are angularly offset with respect to the tubes 7 of the first level.

Besides, several (preferably four) tubes 7 intended to introduce a natural gas-steam mixture open into the third level of the catalytic bed. The flow rate of natural gas is about 95 Nm³/h, and the flow rate of steam is close to 19 Nm³/h. The mixture is introduced at about 773K.

Finally, the fourth level is more specifically reserved for the introduction of pure oxygen, at about 573K, with a flow rate of 55 Nm³/h. Four tubes are then preferably provided, which have the same features as the tubes at the other levels, that is that they are angularly equidistant and angularly offset with respect to the tubes of level 3.

Preferably, the various levels are equidistant, located each at a distance, measured on the longitudinal axis of the reactor, equal to one sixth of the overall height of catalytic bed 4.

Catalytic bed 4 consists of alternating layers made up respectively of 3.8% of chromium on alpha alumina and of 8.8% of nickel on alpha alumina, as illustrated in FIG. 3. Injection tubes 7 located at the first and third levels of the catalytic bed open preferably into the catalyst containing 8.8% of nickel, whereas tubes 6 located at the second and fourth levels open into the catalyst with 3.8% of chromium.

Preferably, the distance d measured on the longitudinal axis of the reactor, between the fourth level and the end of bed 4 towards outlet 8, is about one third of the overall height of the bed.

At the reactor outlet, in accordance with this example, the temperature of the gases is about 1351K, with the following composition:

| | |
|---|---|
| H₂ | 53.6% |
| H₂O | 18.5% |
| CH₄ | 0.6% |
| CO | 23.2% |
| CO₂ | 4.1% |

In this example, one should notice that the carbon dioxide content is higher than the specifications of a synthesis known as Fisher-Tropsch synthesis. A decarbonation process will allow this content to be reduced. The separated carbon dioxide may be advantageously introduced in place of part of the steam.

Other modifications or additions may of course be provided by the man skilled in the art to the reactors described above by way of example, without departing from the scope of the invention.

We claim:

1. A process for producing synthetic gas within a reactor containing a non-catalytic combustion chamber and a catalytic bed within a single housing, said process comprising introducing fuel into said combustion chamber, introducing oxidizer into said combustion chamber, effecting partial combustion of the fuel in the combustion chamber with the oxidizer within said single housing, the fuel being introduced separately from the oxidizer into said chamber, introducing additional oxidizer into the catalytic bed located downstream from said combustion chamber within said single housing, further introducing additional fuel into said catalytic bed upstream from location of the introduction of the additional oxidizer, wherein said combustion chamber has a residence time for the oxidizer and the fuel and an inner volume V for said combustion chamber which satisfy the inequality $$V > 0.4 \, D/P,$$

D being the overall weight flow of materials including fuel and oxidizer entering the combustion chamber, expressed in kg/s, P being the pressure prevailing inside the chamber, expressed in megapascals, and V being expressed in cubic meters, fuel introduced into the reactor consisting essentially of hydrocarbons admixed with carbon oxides and/or hydrogen, and steam being introduced into at least one of the combustion chamber and the catalytic bed, with the steam supply to the reactor, defined by the number of moles of water introduced into the reactor in relation to the number of moles of carbon introduced, being less than 1.5.

2. A process as claimed in claim 1, wherein said single housing contains the combustion chamber equipped with at least one fuel injection element and at least one oxidizer injection element for introducing the fuel and the oxidizer, respectively, into said combustion chamber in order to effect partial combustion of the fuel within said chamber, and at least one catalytic bed into which gases discharged from the combustion chamber flow and at least one additional oxidizer injection element for introducing the additional oxidizer into said at least one catalytic bed and at least one additional fuel injection element opening into said catalytic bed upstream from the one additional oxidizer injection element for introducing the additional fuel into the catalytic bed; steam being introduced into the combustion chamber via at least one of the fuel injection element and the oxidizer injection element and into the catalytic bed via the at least one additional oxidizer injection element or the at least one additional fuel injection element.

3. A process according to claim 1, wherein the hydrogen/hydrocarbon ratio, defined by the molar ratio expressed in the number of moles of hydrogen to the number of moles of carbon in the hydrocarbon fuel introduced into the combustion chamber, is less than 1.

4. A process according to claim 1, wherein the oxidizer is selected from the group consisting of pure oxygen, a mixture of oxygen and nitrogen, a mixture of oxygen and steam, a mixture of oxygen and carbon dioxide, and a mixture of oxygen and another inert gas.

5. A process according to claim 1, wherein the fuel is preheated before entering the combustion chamber to temperatures between 100° and 850° C. and wherein the oxidizer is preheated before entering the combustion chamber to temperatures between 100° and 900° C.

6. A process according to claim 1, wherein the overall oxidizer supply, defined as the number of moles of oxygen contained in the oxidizer injected into the reactor in relation to the number of moles of carbon contained in the injected fuel, ranges between 0.3 and 0.65 and wherein the same supply relative to the introduction of oxidizer in said combustion chamber ranges between 0.45 and 0.75.

* * * * *